United States Patent [19]

Singleton et al.

[11] Patent Number: 5,221,286

[45] Date of Patent: Jun. 22, 1993

[54] COLD MIX EMULSIONS USED AS A DEVELOPER COMPOSITION FOR OXIDATIVE HAIR DYES AND FOR HAIR BLEACHES

[75] Inventors: A. H. Singleton; S. N. Porter, both of Kingsport, Tenn.

[73] Assignee: Eastman Kodak Company, Rochester, N.Y.

[21] Appl. No.: 914,123

[22] Filed: Jul. 17, 1992

[51] Int. Cl.$^5$ .................... A61K 7/13; A61K 47/00; C11D 3/395
[52] U.S. Cl. ............................................ 8/406; 8/405; 252/94; 252/DIG. 13; 514/846; 514/943; 514/786; 424/62; 424/70
[58] Field of Search ................. 252/183.15, DIG. 13, 252/94; 514/844, 845, 846, 943, 786; 424/62, 70; 8/405, 406

[56] References Cited

U.S. PATENT DOCUMENTS

| | | | |
|---|---|---|---|
| 4,685,931 | 8/1987 | Schieferstein et al. | 8/406 |
| 4,834,767 | 5/1989 | Helioff et al. | 8/416 |
| 4,927,627 | 5/1990 | Schrader et al. | 424/62 |

*Primary Examiner*—Paul Lieberman
*Assistant Examiner*—Michael P. Tierney
*Attorney, Agent, or Firm*—John D. Thallemer; William P. Heath, Jr.

[57] ABSTRACT

This invention relates to a nonionic cold mix emulsion and preparation thereof. More particularly, the present invention relates to a cosmetic composition in the form of a cream preparation which comprises a discontinuous phase dispersed in a continuous phase. The continuous phase contains water, an emulsifier, and at least one oxidizing agent. The discontinuous phase contains salts of fatty acid esters of lactylic acid, saturated monoglycerides and propylene glycol monoesters. The emulsions are particularly suitable as components of oxidizing preparations for the bleaching of hair and for the dying of hair with oxidation hair dyes and hair bleaches.

17 Claims, No Drawings

COLD MIX EMULSIONS USED AS A DEVELOPER COMPOSITION FOR OXIDATIVE HAIR DYES AND FOR HAIR BLEACHES

FIELD OF THE INVENTION

This invention relates to a nonionic cold mix emulsion and preparation thereof. More particularly, the present invention relates to a cosmetic composition in the form of a cream preparation which comprises a discontinuous phase dispersed in a continuous phase. The continuous phase contains water, an emulsifier, and at least one oxidizing agent. The discontinuous phase contains salts of fatty acid esters of lactylic acid, saturated monoglycerides and propylene glycol monoesters. The emulsions are particularly suitable as components of oxidizing preparations for the bleaching of hair and for the dying of hair with oxidation hair dyes and hair bleaches.

BACKGROUND OF THE INVENTION

The main coloring component of hair is a dark pigment, melanin, which occurs as granules embedded in the hair cortex. The aim of bleaching is to decolorize selectively the pigments in the hair with minimal damage to the hair matrix. When hair is bleached, the color changes to lighter and lighter shades depending upon the amount of melanin granules dissolved and removed from the hair fiber. More specifically, bleaching occurs in two steps: (1) initial solubilization of the color granules and (2) decolorization of the dark brown solubilized pigment. The reaction between melano-protein and oxidizing compound is confined mainly to the protein-combined cystene residues which are subsequently converted to combined cysteic acid. The solubilization of the melanin granules is connected with the splitting of the disulfide bridges in the melano protein.

The bleaching process can be halted at any point or can be permitted to continue to a light blonde or platinum shade. The latter provides a good background for a variety of tints which can be obtained by a subsequent coloring step. Such bleaching and coloring combination is known as a double process coloring and causes hair damage by promoting porosity, brittleness, dryness and loss of tensile strength. Problems are encountered when the consistency of the dye or bleach preparation is too low, particularly the problem of the dye or bleach preparation running along the hair and causing undesired dyeing or bleaching of certain parts of the hair.

It has long been known that alkali-soluble acrylate dispersions may be used for thickening aqueous systems. U.S. Pat. No. 4,685,931 discloses an aqueous dispersion of a copolymer of ethyl acrylate, methacrylic acid, acrylic acid and a polyethylenically unsaturated copolymerizable monomer. The polyethylenically unsaturated copolymerizable monomer increases the molecular weight of the copolymers and hence their thickening effect. These known copolymer dispersions, however, do not completely satisfy the stringent demands needed for effective thickening, particularly when the dispersions are used in cosmetic preparations. Dispersions of these copolymers, for example, have a marked tendency towards viscosity drift. Additionally, some dispersions show only moderate thickening power; while with other dispersions, the viscosities of the thickened preparations are extremely sensitive to other ingredients in the ultimate formulation.

Particular stringent demands are made of alkali soluble acrylate copolymer dispersions used for thickening hydrogen peroxide preparations. Preparations of this type are commonly employed as developer compositions for oxidative hair dyes and for hair bleaches. The mildly acidic preparations are mixed with an alkaline dye cream just before application to the hair to form an alkaline dye preparation. Since this destroys the consistency of the cream, a thickener dispersion is included in the developer preparation in order to achieve a mixture viscosity suitable for applying the alkaline dye preparation to hair after the two components have been combined.

Alkali soluble carboxyl-group containing polymers have been used for thickening emulsions. U.S. Pat. No. 4,927,627 discloses a oil-in-water emulsion which contains a oil component, an emulsifier, hydrogen peroxide and a carboxyl-group containing polymer. Such carboxyl-group containing polymer dispersions, however, have a marked tendency towards viscosity drift.

In contrast, the present invention has overcome the above deficiencies without resorting to thickening agents, by providing a stable emulsion containing an oxidizing agent which maintains a viscosity suitable for uniform application to hair. In addition, the emulsion of the present invention, conditions the hair during processing and is prepared at room temperature. The present inventors have unexpectedly discovered that the incorporation of a food grade emulsifier into an emulsion used as the developer composition for oxidative hair dyes and for hair bleaches serves a dual function of stabilizing the viscosity as well as emulsification.

SUMMARY OF THE INVENTION

Accordingly, it is one object of the present invention to provide a stable emulsion containing an oxidizing agent which maintains a viscosity suitable for uniform application to hair.

Another object of this invention is to provide a stable emulsion composition which contains an oxidizing agent and is prepared at room temperature.

These and other objects are accomplished herein by a nonionic cold mix emulsion comprising:

(I) about 99 to about 90 weight percent of a continuous phase comprising
  (a) about 20 to about 95 weight percent of water;
  (b) about 2 to about 35 weight percent of at least one oxidizing agent for liberating active oxygen, calculated as hydrogen peroxide; and
  (c) about 1 to about 6 weight percent of at least one emulsifier; and (II) about 1 to about 10 weight percent of a discontinuous phase comprising
  (d) about 8.8 to about 20 weight percent of at least one salt of a fatty acid ester of lactylic acid;
  (e) about 29.8 to about 39.2 weight percent of at least one saturated monoglyceride of a straight chain fatty acid having from 8 to 22 carbon atoms and an iodine value of 0 to about 20; and
  (f) about 41.2 to about 52.0 weight percent of at least one saturated monoester of propylene glycol and a straight chain fatty acid having from 8 to 2 carbon atoms and an iodine value of 0 to about 20.

DESCRIPTION OF THE INVENTION

The emulsions of the present invention contain a continuous phase (I) which is present in an amount of from about 99 to about 90 weight percent of the emulsion. The continuous phase contains about 20 to about 95 weight percent of water. Preferably, the water is present in an amount of from 70 to 80 weight percent of the total emulsion composition. Tap water or distilled water may be used, however, distilled or deionized water is preferred. The water can be partially replaced by up to 30 weight percent of an alcohol. Such alcohols may include glycerol, methanol, ethanol, sorbitol, isopropanol, ethylene glycol, propylene glycol, or mixtures thereof.

The second component of the continuous phase is at least one oxidizing agent for liberating active oxygen. Suitable examples of oxidizing agents which liberate active oxygen include, for example, hydrogen peroxide, precarbamide, hydroquinone, alkali metal salts of perborate, alkali metal salts of percarbonate such as the sodium salt, melamine perhydrate, and alkali metal persulfate. The oxidizing agent portion of the composition of the invention may consist of one or more of such per compounds. The amount of the oxidizing agent is based upon the total weight of the emulsion and may vary from 2 to 35 percent, when calculated as pure hydrogen peroxide.

In formulations for bleaching and coloring hair, the preferred oxidizing agent is hydrogen peroxide. The hydrogen peroxide may be any commercially available form of hydrogen peroxide which is diluted down to about 2 to about 35 weight percent. The composition preferably contains 4 to 7 weight percent hydrogen peroxide. The reason for preferring lower amounts of hydrogen peroxide is not particularly because of stability or performance, but because of safety and ease of use. Hydrogen peroxide solutions usually take the form of stabilized 5 percent hydrogen peroxide solutions. Such solutions are commercially available from DuPont Chemical Company, ALBONE 35 CG, and from FMC Chemical Company, Standard 35% $H_2O_2$ or SUPER D 35% $H_2O_2$.

The third component of the continuous phase is an emulsifier, component (c). The emulsifier acts effectively to combine the different components of the composition to give a stable uniform blend. The emulsifier is present in an amount of from 0.5 to 20 weight percent. Numerous emulsifiers and mixtures of emulsifiers may be used to assist in maintaining the emulsions of the present invention. The preferred emulsifiers include: acetylated monoglycerides, for example the acetylated monoglyceride composition available under the trade name MYVACET 9-45 by Eastman Chemical Products, Inc.; polyethylene glycol-8-oleate compositions such as those available under the trade name WITCONOL H31A by Witco Chemical Company; and hydrophilic ethoxylated sorbitan monoesters such as sorbitan monostearate plus 20 moles of ethylene oxide, TWEEN 60 and GLYCOSPERSE S-20 FG, sorbitan mono oleate plus 20 moles of ethylene oxide, TWEEN 80, sorbitan laurate plus 20 moles of ethylene oxide, TWEEN 20; lecithin, monoglycerides (MYVEROL), and diglycerides. The TWEEN compounds are commercially available from ICI America and GLYCOSPERSE S-20 FG is commercially available from Lonza Chemical Co. MYVEROL distilled monoglycerides are commercially available from Eastman Chemical Products, Inc., for example, MYVEROL 18-00, 18-04, 18-06, 18-07, 18-50, 18-85, and 18-92. The present inventors have determined that a mixture of the emulsifiers are preferred over the use of such emulsifiers individually.

It has been determined that within the given classes of emulsifiers outlined above, effective emulsifiers may be identified by their hydrophile-lipophile balance (HLB) values. HLB expresses on a numerical scale the relative behavior of an emulsifier towards oil and towards water, as experimentally determined. The numerical scale is defined by arbitrarily assigning a value of 1.0 to oleic acid and a value of 20 to potassium oleate. An important principle inherent in the HLB concept is that the HLB value of a mixture of emulsifiers will equal the weighted average of the HLB values of its individual component emulsifiers. For purposes of the present invention the emulsifier (c) or blend of emulsifiers should have a combined HLB of less than 12.0 and preferably less than 10.0. For example, a preferred blend of emulsifiers is a 50/50 blend of TWEEN 60 which has an HLB of 14.9 and MYVACET 9-45 which has an HLB of 3.8. The weighted average of the HLB values of the 50/50 blend of TWEEN 60 and MYVACET 9-45 is about 9.4.

The discontinuous phase (II) of the present invention contains salts of fatty acid esters of lactylic acid, component (d), saturated monoglycerides, component (e), and propylene glycol monoesters, component (f). The discontinuous phase is present in emulsion compositions in an amount of about 1.0 to about 10.0 weight percent. Preferably, the emulsions of the present invention contain 3.0 to 8.0 weight percent of the discontinuous phase (II).

Component (d) is at least one salt of a fatty acid ester of lactylic acid, and is present in an amount of about 8.8 to about 20.0 weight percent of the discontinuous phase (II). Salts of fatty acid esters of lactylic acid employed in the invention are well known in the art and available commercially. They may be prepared by reacting lactylic acid with acids by known conventional condensation processes. Illustrative of such salts are alkali, alkaline earth, ammonium, and in particular, the sodium, potassium, and calcium salts of fatty acid esters wherein the fatty acid contains 14 to 22 carbon atoms. Such fatty acids include palmitic, stearic, oleic and the like. Particularly preferred are sodium stearoyl-2-lactylate and calcium stearoyl-2-lactylate.

Component (e) is at least one saturated monoglyceride of a straight chain fatty acid having from 8 to 22 carbon atoms and an iodine value of 0 to about 20, and is present in an amount of about 29.8 to about 39.2 weight percent of the discontinuous phase (II). The saturated monoglycerides useful in the present invention preferably have an iodine value of 0 to 5. Preferred saturated monoglycerides also include those made by interesterification of glycerine with fully saturated fats or oils such as tallow, palm oil, cottonseed oil, soybean oil, peanut oil, sesame oil and the like. These monoglycerides usually contain monoesters at a concentration of at least 90% by weight.

Component (f) is at least one saturated monoester of propylene glycol and a straight chain fatty acid having from 8 to 22 carbon atoms and an iodine value of 0 to about 20, and is present in an amount of about 41.2 to about 52.0 weight percent of the discontinuous phase (II). The propylene glycol monoester should be 1,2-propylene glycol monoester, and preferably have an iodine value of 0 to 5. The monoester is advantageously purified after usual preparation by molecular distillation. Stearic acid is the preferred fatty acid moiety of the ester, but other fatty acid moieties deriving from fully hydrogenated oils and fats, which after hydrogenation posses a high content of stearic acid are also useful. Unsaturated fatty acid moieties are not suitable. Examples of fats and oils from which the propylene glycol monoester can be derived are soybean oil, cottonseed oil, lard, and tallow. Hydrogenation of the fatty acid moieties can be performed before or after formation of the propylene glycol monoester. Their principle fatty acid constituent after hydrogenation is stearic acid.

Preferably, the discontinuous phase (II) contains about 10.0 to about 14.0 weight percent of at least one salt of a fatty acid ester of lactylic acid, about 35.0 to about 39.0 weight percent of at least one saturated monoglyceride of a straight chain fatty acid having from 8 to 22 carbon atoms and an iodine value of 0 to about 20, and about 49.0 to about 52.0 weight percent of at least one saturated monoester of propylene glycol and a straight chain fatty acid having from 8 to 22 carbon atoms and an iodine value of 0 to about 20.

In preparing the discontinuous phase (II) of this invention, (a) the salt of fatty acid ester of lactylic acid, (b) saturated monoglyceride, and (c) propylene glycol monoester must be melt blended, and preferably powdered prior to use in the formulation. Such powdered blends are commercially available as MYVATEX TEXTURE LITE food grade emulsifier, available from Eastman Chemical Products, Inc.

An acid may optionally be added to the emulsions of the present invention to control the pH of the emulsions and to enhance stability. The amount of acid used depends on the pH of the emulsion. A pH in the range of 1.8 to 4.0 is preferred. Most preferably the pH is in the range of 2.2 to 3.2 to enhance stability. Any suitable acid may be used for this purpose, for example, phosphoric acid, lactic acid, citric acid, tartaric acid, maleic acid, hydroxysuccinic acid or mixtures thereof. Occasionally an acid is not required to bring the composition to within the range of 1.8 to 6.5, however, it is generally necessary and in fact preferred to incorporate at least one acid into the emulsion compositions.

Other non-essential additives which are common to cosmetic formulations of the art may be incorporated into the emulsions of this invention provided they do not destabilize the emulsions so as to cause a breaking or an inverting of the emulsion. Such non essential additives include: carriers, detergents, foaming agents, conditioners, chelating agents, lustering agents, fragrances, perfumes, humectants, preservatives, colorants, oxidation dye intermediates, pharmaceutically active quinoline derivatives, urea, hydrocortisone and chelating agents. All of these additives and the use thereof are well known in the art.

The emulsions of the present invention are prepared by preparing, separately, the indicated continuous phase (I) and the indicated discontinuous phase (II) and then slowly adding the discontinuous phase to the agitated continuous phase, followed by continued agitation of the resulting mixture until it becomes homogeneous. Agitation is accomplished by a propeller mixer or a homogenizer. Other methods of emulsion preparation which provide stable oil in water emulsions are suitable, but care must be taken to prevent inversion of the emulsion to an water in oil emulsion during its preparation.

The emulsions prepared in this manner may be formulated into creams, gels or solutions which are used in the cosmetic field on hair and skin. The emulsions are particularly suitable as components of oxidizing preparations for the bleaching of hair and for the dying of hair with oxidation hair dyes and hair bleaches. The emulsions may be employed for changing the color of hair, covering up white hair, shading the hair after lightening or simultaneous bleaching and dyeing or double process blonding to provide color alteration of long color durability.

A process for bleaching human hair using the emulsions of the present invention involves applying directly to the hair an effective amount of the emulsions at a temperature ranging from about 15° C. to about 40° C. for a time sufficient to bleach the hair. The amount of emulsion needed depends on many factors including the amount and density of hair, the concentration of the emulsion, and the degree of bleaching desired, thus the term "effective amount".

The materials and testing procedures used for the results shown herein are as follows:

The iodine values specified herein are measured in accordance with AOCS Official Method Cd 1-25, Official and Tentative Methods of the American Oil Chemists Society, 2nd ed., additions and revisions 1947 through 1963, inclusive.

The invention will be further illustrated by a consideration of the following examples, which are intended to be exemplary of the invention. All parts and percentages in the examples are on a weight basis unless otherwise stated.

EXAMPLE 1

Preparation of Discontinuous Phase (II)

The following ingredients were melt blended using a Model N-50 Hobart Mixer: 12.0 grams of the sodium salt of stearoyl-2-lactylic acid, 37.0 grams saturated monoglyceride, and 51.0 grams propylene glycol monoesters. The blend was spray chilled and silicone dioxide was added to form a free flowing powder.

EXAMPLE 2

Preparation of Continuous Phase

The following ingredients were combined: 74.86 grams of distilled water, 17.14 grams of a 35% hydrogen peroxide solution, 3.0 grams of a 50/50 weight percent blend of sorbitan monostearate plus 20 moles of ethylene oxide and MYVACET 9-45.

EXAMPLE 3

Preparation of Emulsion Composition

The discontinuous phase prepared in Example 1, 5.0 grams, was slowly added to the continuous phase prepared in Example 2 while agitation was applied to the continuous phase by means of a propeller mixer. Agitation was continued until homogeneous. The pH of the emulsion was adjusted to about 3.0 by the addition of concentrated phosphoric acid. The emulsion contained 6.0 percent hydrogen peroxide and was stable for longer than one year.

EXAMPLE 4

Preparation of Emulsion Composition

A continuous phase was prepared by combining the following ingredients: 74.86 grams of distilled water, 17.14 grams of a 35% hydrogen peroxide solution, 3.0 grams of a 60/40 weight percent blend of sorbitan monostearate plus 20 moles of ethylene oxide and MYVACET-9-45.

The discontinuous phase prepared in Example 1, 5.0 grams, was slowly added to the continuous phase while agitation was applied to the continuous phase by means of a propeller mixer. Agitation was continued until homogeneous. The pH of the emulsion was adjusted to about 3.0 by the addition of concentrated phosphoric acid. The emulsion contained 6.0 percent hydrogen peroxide and was stable for longer than one year.

EXAMPLE 5

Preparation of Emulsion Composition

A continuous phase was prepared by combining the following ingredients: 74.86 grams of distilled water, 17.14 grams of a 35% hydrogen peroxide solution, 3.0 grams of a 70/30 weight percent blend of sorbitan monostearate plus 20 moles of ethylene oxide and MYVACET-9-45.

The discontinuous phase prepared in Example 1, 5.0 grams, was slowly added to the continuous phase while agitation was applied to the continuous phase by means of a propeller mixer. Agitation was continued until homogeneous. The pH of the emulsion was adjusted to about 3.0 by the addition of concentrated phosphoric acid. The emulsion contained 6.0 percent hydrogen peroxide and was stable for longer than one year.

Many variations will suggest themselves to those skilled in this art in light of the above detailed description. All such obvious modifications are within the full intended scope of the appended claims.

What is claimed is:

1. A nonionic cold mix cream emulsion bleach comprising:
   (I) about 99 to about 90 weight percent of a continuous phase comprising
      (a) about 20 to about 95 weight percent of water;
      (b) about 2 to about 35 weight percent of at least one oxidizing agent for liberating active oxygen, calculated as hydrogen peroxide; and
      (c) about 1 to about 6 weight percent of at least one emulsifier; and
   (II) about 1 to about 10 weight percent of a discontinuous phase comprising
      (d) about 8.8 to about 20 weight percent of at least one salt of a fatty acid ester of lactylic acid;
      (e) about 29.8 to about 39.2 weight percent of at least one saturated monoglyceride of a straight chain fatty acid having from 8 to 22 carbon atoms and an iodine value of 0 to about 20; and
      (f) about 41.2 to about 52.0 weight percent of at least one saturated monoester of propylene glycol and a straight chain fatty acid having from 8 to 22 carbon atoms and an iodine value of 0 to about 20.

2. The emulsion of claim 1 wherein the water, component (a), is present in an amount of from 70 to 80 weight percent of the total emulsion.

3. The emulsion of claim 2 wherein the water, component (a), is present in an amount of from 73 to 76 weight percent of the total emulsion.

4. The emulsion of claim 1 wherein the oxidizing agent, component (b) is selected from the group consisting of hydrogen peroxide, hydroquinone, percarbamide, an alkali metal perborate, an alkali metal percarbonate, melamine perhydrate, an alkali metal persulfate and mixtures thereof.

5. The emulsion of claim 4 wherein the oxidizing agent is hydrogen peroxide.

6. The emulsion of claim 1 wherein the oxidizing agent, component (b) is present in an amount of from 4 to 9 weight percent, calculated as hydrogen peroxide.

7. The emulsion of claim 1 wherein the emulsifier, component (c) is selected from the group consisting of a mixture of distilled propylene glycol monoesters, distilled monoglycerides and sodium stearyl lactylate, hydrophilic ethoxylated sorbitan monoesters, malto dextrin, lecithin, monoglycerides, diglycerides, and mixtures thereof.

8. The emulsion of claim 7 wherein the hydrophilic ethoxylated sorbitan monoesters are selected from the group consisting of sorbitan monostearate plus 20 moles of ethylene oxide, sorbitan monooleate plus 20 moles of ethylene oxide, sorbital laurate plus 20 moles of ethylene oxide, and mixtures thereof.

9. The emulsion of claim 1 wherein the discontinuous phase (II) consists essentially of:
   (d) 10.0 to 14.0 weight percent of at least one salt of a fatty acid ester of lactylic acid;
   (e) 35.0 to 39.0 weight percent of at least one saturated monoglyceride of a straight chain fatty acid having from 8 to 22 carbon atoms and an iodine value of 0 to about 20; and
   (f) 49.0 to 52.0 weight percent of at least one saturated monoester of propylene glycol and a straight chain fatty acid having from 8 to 22 carbon atoms and an iodine value of 0 to about 20.

10. The emulsion of claim 1 wherein the salt of a fatty acid ester of lactylic acid is an alkali, alkaline earth or ammonium salt.

11. The emulsion of claim 10 wherein the salt of a fatty acid ester of lactylic acid is a sodium, potassium or calcium salt.

12. The emulsion of claim 1 which additionally contains an acid selected from the group consisting of phosphoric acid, lactic acid, citric acid, tartaric acid, maleic acid, hydroxysuccinic acid and mixtures thereof.

13. The emulsion of claim 12 wherein the acid is phosphoric acid.

14. A method of preparing a nonionic cold mix cream emulsion bleach comprising:
   (I) about 99 to about 90 weight percent of a continuous phase comprising
      (a) about 20 to about 95 weight percent of water;
      (b) about 2 to about 35 weight percent of at least one oxidizing agent for liberating active oxygen, calculated as hydrogen peroxide; and
      (c) about 1 to about 6 weight percent of at least one emulsifier; and
   (II) preparing a discontinuous phase comprising
      (d) about 8.8 to about 20 weight percent of at least one salt of a fatty acid ester of lactylic acid;
      (e) about 29.8 to about 39.2 weight percent of at least one saturated monoglyceride of a straight chain fatty acid having from 8 to 22 carbon atoms and an iodine value of 0 to about 20; and
      (f) about 41.2 to about 52.0 weight percent of at least one saturated monoester of propylene glycol and a straight chain fatty acid having from 8 to 22 carbon atoms and an iodine value of 0 to about 20; and
   (III) combining (I) and (II) to thereby obtain an emulsion.

15. A process for the bleaching of human hair consisting essentially of applying to said hair at a temperature ranging from about 15° C. to 40° C. for a time sufficient to bleach said hair, an effective amount of the emulsion according to claim 1.

16. A substrate having the emulsion composition of claim 1 deposited thereon.

17. A dermatological composition in the form of a cream preparation prepared by the process according to claim 14.

* * * * *